(12) United States Patent
Morita et al.

(10) Patent No.: US 7,127,684 B2
(45) Date of Patent: Oct. 24, 2006

(54) SYNCHRONIZED MAGNIFICATION SYSTEM AND METHOD FOR IMAGES

(75) Inventors: Mark M. Morita, Arlington Heights, IL (US); Steven L. Fors, Chicago, IL (US); C. Cameron Brackett, Naperville, IL (US)

(73) Assignee: GE Informational Systems Technologies, Inc., Milwaukee, WI (US)

( * ) Notice: Subject to any disclaimer, the term of this patent is extended or adjusted under 35 U.S.C. 154(b) by 746 days.

(21) Appl. No.: 10/304,352

(22) Filed: Nov. 26, 2002

(65) Prior Publication Data

US 2004/0100503 A1 May 27, 2004

(51) Int. Cl.
*G06F 3/00* (2006.01)
(52) U.S. Cl. .............. 715/781; 715/804; 382/132; 382/276; 382/282; 382/283
(58) Field of Classification Search .............. 715/804
See application file for complete search history.

(56) References Cited

U.S. PATENT DOCUMENTS

| | | | | |
|---|---|---|---|---|
| 5,212,637 A | * | 5/1993 | Saxena | 600/407 |
| 5,982,917 A | * | 11/1999 | Clarke et al. | 382/132 |
| 6,243,095 B1 | * | 6/2001 | Shile et al. | 715/854 |
| 6,448,956 B1 | | 9/2002 | Berman et al. | |
| 6,463,181 B1 | * | 10/2002 | Duarte | 382/254 |
| 6,487,271 B1 | * | 11/2002 | Laurent | 378/98.9 |
| 6,630,937 B1 | * | 10/2003 | Kallergi et al. | 345/619 |
| 6,901,561 B1 | * | 5/2005 | Kirkpatrick et al. | 715/863 |
| 2002/0114530 A1 | * | 8/2002 | Duarte | 382/254 |
| 2003/0164860 A1 | * | 9/2003 | Shen et al. | 345/804 |
| 2005/0213801 A1 | * | 9/2005 | Ohara | 382/132 |

* cited by examiner

*Primary Examiner*—Kristine Kincaid
*Assistant Examiner*—Samantha Urban
(74) *Attorney, Agent, or Firm*—Andrus, Sceales, Starke & Sawall

(57) ABSTRACT

A synchronized image manipulation system and method are disclosed. The image manipulation system includes a computer device for controlling the operation of the system, at least one display screen for displaying a plurality of generally similarly shaped objects, and an operator control device for receiving operator input. The plurality of generally similarly shaped objects include a plurality of view ports that display at least a portion of the plurality of generally similarly shaped objects. The operator control device controls the operation of the system in accordance with the operator input and at least one image manipulation function. In addition, the at least one image manipulation function synchronizes the plurality of view ports according to either a mirror synchronization configuration or a symmetrical synchronization configuration.

30 Claims, 9 Drawing Sheets

SYNCHRONIZED MAGNIFICATION SYSTEM AND METHOD FOR IMAGES

BACKGROUND OF THE INVENTION

The field of the invention is imaging methods and systems. More particularly, the invention relates to a synchronized magnification system and method for generally similarly shaped objects.

Digital imaging systems are commonly employed to allow an operator to obtain images that show the interior of a structure of interest. A common application of such imaging systems is medical imaging, and common approaches for implementing such imaging systems, especially in the context of medical imaging, include magnetic resonance imaging, ultrasound imaging, X-ray imaging, computerized tomography, etc.

Today, many tools exist that assist operators when using digital imaging systems. For example, operators often need to define a particular region in a view port and create a mask around this area. This allows an operator to focus clearly within the defined region so that extraneous imagery does not distract the eye. For many operators, particularly radiologists, there exists a need to frequently manipulate and reconfigure masked images within a short period of time. Consequently, it is desirable to have a system that allows operators to interactively navigate through images as well as create, manipulate, and reconfigure masks in real-time.

In many instances, particularly screening mammography, it would be desirable for radiologists to be able to compare zoomed regions in multiple image ports simultaneously. Mammographers are taught to scan right breast images counter clockwise and left breast images in a clockwise fashion. Thus, it would be advantageous if mammographers had the ability to compare multiple zoomed regions in mirrored or symmetrical synchronization. Consequently, it is desirable to have a system that allows an operator to interactively view, magnify, and inspect multiple image ports simultaneously, in symmetrical and mirrored synchronization.

SUMMARY OF THE INVENTION

One embodiment of the invention provides an image masking system including a computer device, at least one display screen, and an operator control device. The computer device controls the operation of the system. The at least one display screen is coupled to the computer device and displays at least one image. The image includes at least one view port that displays at least a first portion of the at least one image and at least one masking region that displays at least a second portion of the at least one image. The operator control device is coupled to the computer device for receiving operator input. The operator input is provided to the computer device so that the computer device controls operation of the system in accordance with the operator input and at least one image manipulation function, including a real-time masking function. The real-time masking function permits the at least one masking region to be reconfigured in real-time while continuously displaying the at least one masking region and the at least one view port.

Another embodiment of the invention provides an image masking system including a computer device, at least one display screen, and an operator control device. The computer device controls operation of the system. The at least one display screen is coupled to the computer device for displaying a plurality of radiology images. The plurality of radiology images include view ports that display at least a first portion of the at least one of the plurality of radiology images. The plurality of radiology images also include a plurality of masking regions that display at least a second portion of at least one of the plurality of radiology images. The operator control device is coupled to the computer device for receiving operator input being provided to the computer device to permit the computer device to control operation of the system in accordance with the operator input and at least one image manipulation function. The at least one image manipulation function synchronizes the plurality of view ports according to a mirror synchronization configuration and includes a real-time masking function.

Another embodiment of the invention provides an image masking system including a computer device, at least one display screen, and an operator control device. The computer device controls operation of the system. The at least one display screen is coupled to the computer device for displaying a plurality of radiology images. The plurality of radiology images include view ports that display at least a first portion of the at least one of the plurality of radiology images. The plurality of radiology images also include a plurality of masking regions that display at least a second portion of at least one of the plurality of radiology images. The operator control device is coupled to the computer device for receiving operator input being provided to the computer device to permit the computer device to control operation of the system in accordance with the operator input and at least one image manipulation function. The at least one image manipulation function synchronizes the plurality of view ports according to a symmetrical synchronization configuration and includes a real-time masking function.

Another embodiment of the invention provides a method of masking at least a portion of an image. The method includes displaying at least one image on at least one display screen. The method also includes receiving operator input to configure the at least one image. In addition, the method includes defining one or more areas on the at least one image as one or more view ports, and defining the remaining areas on the at least one image as one or more masking regions. Further, the method includes at least partially masking the one or more masking regions in real-time according to at least one image manipulation function where the at least one image manipulation function comprises a real-time masking function. The real-time masking function permits the one or more masking regions to be reconfigured in real-time while continuously displaying the plurality of masking regions and the one or more view ports.

Another embodiment of the invention provides an image masking system including a means for controlling the operation of the system. Also, the system includes a means for displaying at least one image where the at least one image includes at least one masking region and at least one view port. The at least one masking region is at least partially masked and the at least one view port displays at least a portion of the at least one image. In addition, the system includes a means for receiving operator input. Further, the system includes a means for configuring the at least one masked region according to at least one image manipulation function including a real-time masking function. The real-time masking function permits the at least one masking region to be reconfigured in real-time while continuously displaying the at least one masking region and the at least one view port.

Further, another embodiment of the invention provides an image manipulation system including a computer device, at least one display screen, and an operator control device. The computer device controls the operation of the system. The at least one display screen is coupled to the computer and displays a plurality of generally similarly shaped objects. The plurality of generally similarly shaped objects include a plurality of view ports that display at least a portion of the plurality of generally similarly shaped objects. The operator control device is coupled to the computer device for receiving operator input. The operator input is provided to the computer device so that the computer device controls operation of the system in accordance with the operator input and at least one image manipulation function. The image manipulation function synchronizes a plurality of view ports according to either a mirror synchronization configuration or a symmetrical synchronization configuration.

Another embodiment of the invention provides an image manipulation system including a computer device, at least one display screen, and an operator control device. The computer device controls operation of the system. The at least one display screen is coupled to the computer device and displays a plurality of mammography images. The plurality of mammography images includes a plurality of view ports that display at least a portion of the plurality of mammography images. Further, the operator control device is coupled to the computer device for receiving operator input. The operator input is provided to the computer device to permit the computer device to control operation of the system in accordance with operator input and at least one image manipulation function. The at least one image manipulation function synchronizes the plurality of view ports according to a mirror synchronization configuration.

Another embodiment of the invention provides an image manipulation system including a computer device, at least one display screen, and an operator control device. The computer device controls operation of the system. The at least one display screen is coupled to the computer device and displays a plurality of mammography images. The plurality of mammography images includes a plurality of view ports that display at least a portion of the plurality of mammography images. Further, the operator control device is coupled to the computer device for receiving operator input. The operator input is provided to the computer device to permit the computer device to control operation of the system in accordance with operator input and at least one image manipulation function. The at least one image manipulation function synchronizes the plurality of view ports according to a symmetrical synchronization configuration.

Another embodiment of the present invention provides a method of manipulating an image including displaying a plurality of generally similarly shaped objects on at least one display screen. The method includes receiving operator input for configuring the plurality of generally similarly shaped objects. In addition, the method includes defining a plurality of areas on the plurality of generally similarly shaped objects as view ports. Further, the method includes synchronizing the view ports according to a synchronization configuration including either a mirror synchronization or symmetrical synchronization. Furthermore, the method includes manipulating the plurality of generally similarly shaped objects according to at least one image manipulation function.

Another embodiment of the present invention provides a system including a means for controlling the operation of the system. In addition, the system includes a means for displaying a plurality of generally similarly shaped objects. The system also includes a means for displaying a plurality of view ports that display at least a portion of the generally similarly shaped objects. Further, the system includes a means for receiving operator input and a means for manipulating the plurality of generally similarly shaped objects according to the operator input. Furthermore, the system includes a means for synchronizing the plurality of view ports according to either a mirror synchronization configuration or a symmetrical synchronization configuration.

DESCRIPTION OF THE PREFERRED EMBODIMENT

Figure 1:
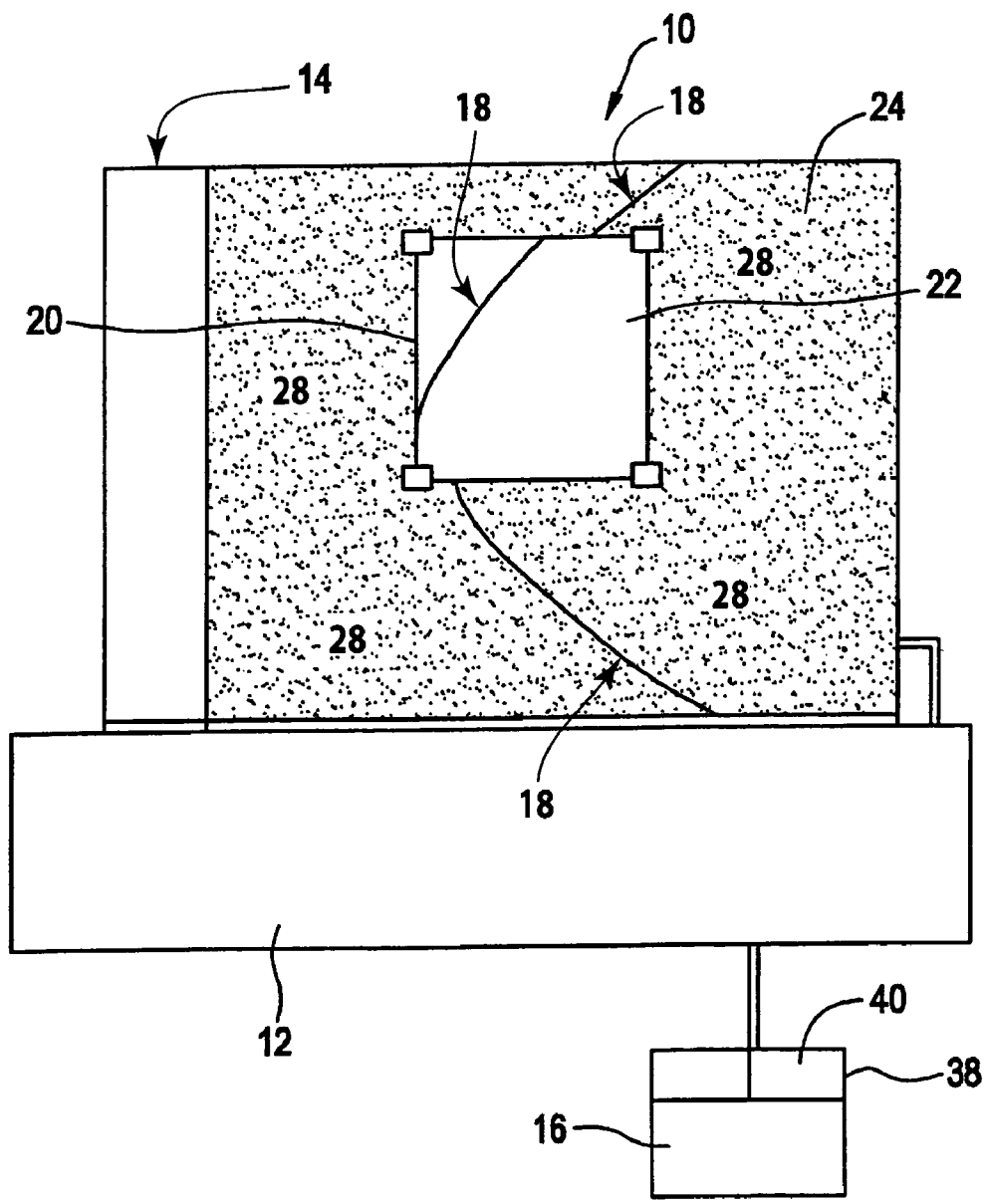
FIG. 1 is a schematic diagram showing a real-time masking system according to an exemplary embodiment.

Referring to FIG. 1, there is shown the major components of an image masking system according to an exemplary embodiment. FIG. 1 shows a computer device 12 for controlling the operation of the image masking system 10. A display 14 is coupled to computer device 12 for displaying at least one image 18. Image 18 may include many different types of objects such as generally similarly shaped objects, radiology images, mammography images, etc. Further, image 18 may include at least one view port 20 that displays at least a first portion 22 image 18. Image 18 may include at least one masking region 26 that displays at least a second portion 24 of the at least one image 18. In addition, FIG. 1 shows an operator control device 12 to permit computer device 12 to control operation of the system 10 in accordance with the operator input and at least one image manipulation function.

As shown in FIG. 1, system 10 may include one display screen 14. Alternatively, system 10 may include a plurality of display screens 14 (e.g., 2 or more display screens). Further, the number of view ports 20 may be limited to one. Alternatively, the number of view ports 20 may be two or more.

The at least one image manipulation function includes a real-time masking function. Real-time masking function permits the at least one masking region 28 to be reconfigured in real-time while continuously displaying the at least one masking region 28 and the at least one view port 20. Therefore, an operator may move view port 20 around image 18 in real-time to focus in on certain areas of image 18 while being able to continuously see view port 20 and masking regidn 28. Further assisting this process is the ability to at least partially mask out the second portion 24 of image 18 to create an at least partially masked region 28 in real-time. Furthermore, the opacity of the late least partially masked region 28 may be configured from 0 to 100% in real-time. In other words, the darkness of the at least partially masked region 28 may be varied according to an operator. For example, if an operator desires to mask part of image 18, but only wants the mask to lightly cover the underlying second portion 24 of image 18, the operator might select a lower opacity setting (e.g., 0 to 33%). Further, if an operator desires to mask part of image 18 somewhat moderately, the operator might select a medium opacity setting (e.g., 33 to 66%). Similarly, if the operator desires a heavy mask, a heavy opacity setting could be selected (e.g., 66 to 100%).

Thus, this feature allows an operator to mask a portion of an image (e.g., unrelated to the examination), but still see an outline of the masked portion under the mask according to the selected opacity setting all in real-time. As used throughout this application, the term "real-time" refers to a level of computer responsiveness that an operator senses as sufficiently immediate or that enables the computer to keep up with some external process (e.g., continuous manipulation of an image by an operator).

Another feature of the real-time masking function 32, is that an operator may select a desired color for the mask. For example, an operator could choose black for the mask. Alternatively, any number of colors could be selected (e.g., green, orange, yellow, blue, purple, etc.). Further, the real-time masking function enables an operator to create/manipulate/configure the masks or underlying portions interactively. In other words, all actions are performed in real-time. Real-time masking function may also be combined with a large number of other functions to manipulate image 18. For example, real-time masking function can work together with a zoom function for zooming in toward and out from at least a portion of image 18, a magnification function for magnifying at least a portion of image 18, a sizing function for increasing or decreasing the size of view port 20, etc. The zoom function, magnification function, sizing function, or other functions are generally controlled by user inputs through the operator control device 16. For example, as shown in FIG. 1, operator control device 16 may include a computer mouse device 38 having at least a right button 40. The image manipulation functions could be configured differently depending on a user by depressing the right button 40 on the computer mouse device 38. Furthermore, system 10 is configured so that any of the image manipulation functions may be conducted interactively in real-time.

Figure 2:
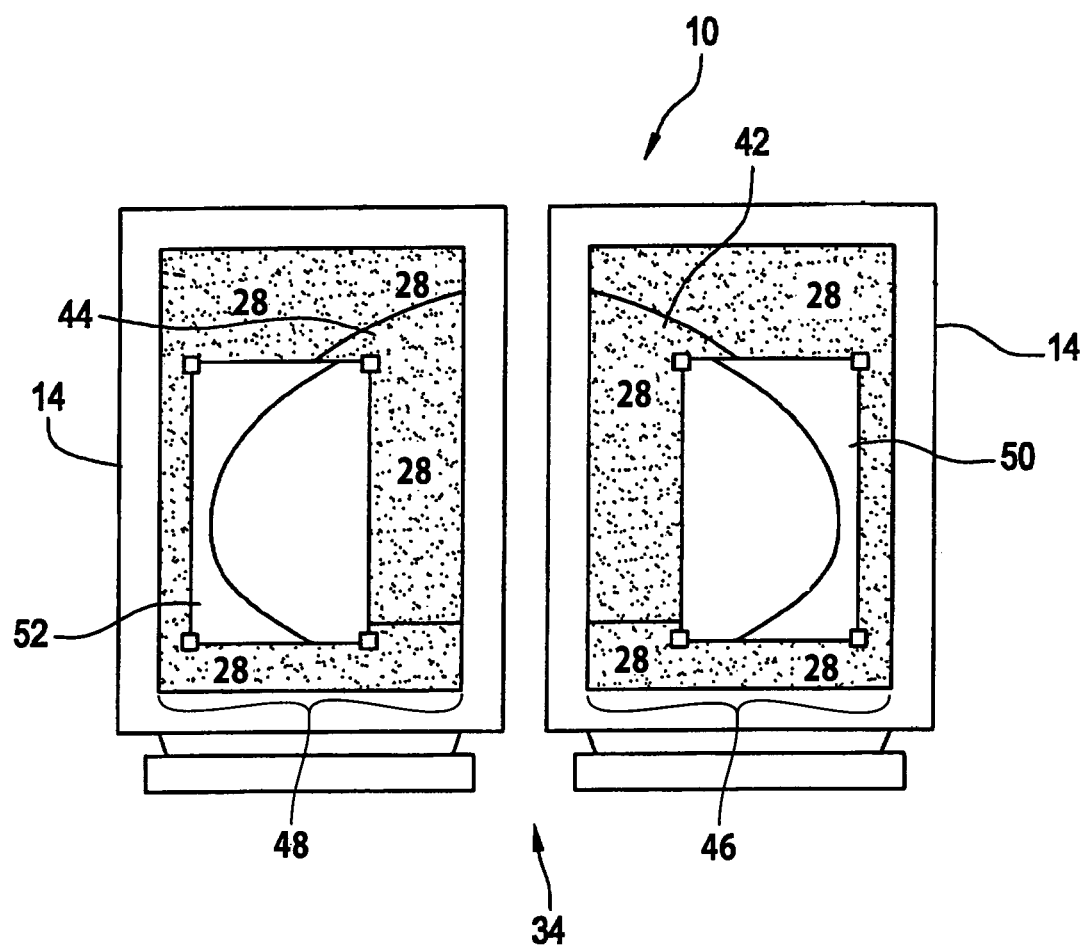
FIG. 2 is a schematic diagram showing dual display screens of a real-time masking system displaying two view ports synchronized based on a mirror synchronization configuration according to an exemplary embodiment.
Figure 3:
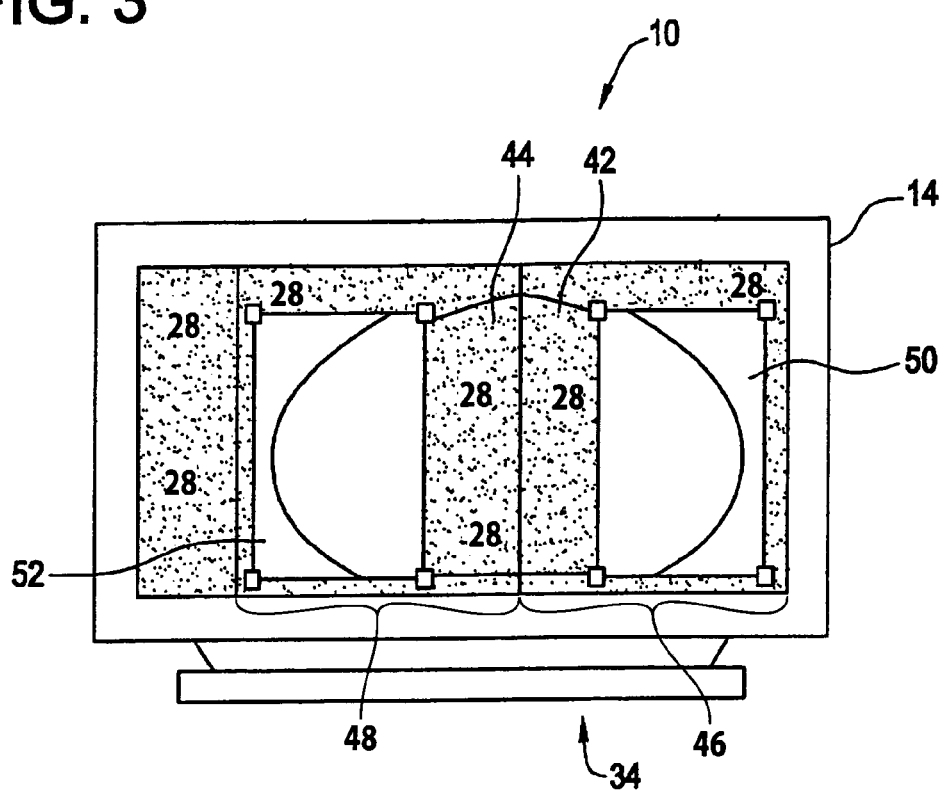
FIG. 3 is a schematic diagram showing a single display screen of a real-time masking system displaying two view ports synchronized based on a mirror synchronization configuration according to an exemplary embodiment.

The at least one image manipulation function may synchronize the plurality of view ports 20 according to either a mirror synchronization configuration 34 or a symmetrical synchronization configuration 36. Mirror synchronization configuration 34 allows a plurality of images 18 to be displayed as mirror images of one another. As shown in FIGS. 2–3, display screen(s) 14 displays a first image 46 of a first object 42. Display screen(s) 14 also displays a first view port 50 that includes at least a portion of the first object 42. Further, display screen(s) 14 displays a second image 48 of a second object 44. Display screen(s) 14 also displays a second view port 52 that includes at least a portion of second object 44. Mirror synchronization configuration 34 orients first image 46 and second image 48 in a mirrored relationship with one another. In addition, mirror synchronization configuration 34 configures first image 46 and the second image 48 so that the movement of first view port 50 mirroredly corresponds to the movement of second view port 52. In other words, mirror synchronization configuration 34 causes view port 50 and view port 52 to be linked in a way that results in one view port mirroring the actions of the other view port (e.g., movement, orientation, manipulation, etc.).

For example, as shown in FIG. 3, as first view port 50 is moved upward along first object 42, the second view port 52 mirroredly (i.e., like a mirror image) moves upward along the second object 44. In addition, as first view port 50 is moved upward, the masked region 28 also moves to correspond to the new location of the first view port 50. In other words, the masked region 28 does not remain static and in fact moves relative to the new location of the first view port 50. This way, an operator can interactively select the areas to be viewed (and at the same time the areas to be masked) by moving the first view port around image 18. The mirror synchronization configuration 34 also configures the second view port 52 to mirroredly move around image 18 in response to any movement of the first view port 50. Therefore, the mirror synchronization configuration enables a user to view two objects in two view ports and/or two images as mirror images of each other while masking less important areas. This feature is particularly useful for radiologists who must quickly compare adjacent current and/or historical images by comparing anatomical regions within the corresponding view ports 50 and 52. Rather than having to locate a landmark in one view port, note it and then take a similar location in the adjacent view port and note it, they have the ability to compare the mirrored regions simultaneously. The radiologist can mask out extraneous regions and focus on specific areas without the contrast or brightness interference from other areas.

Figure 4:
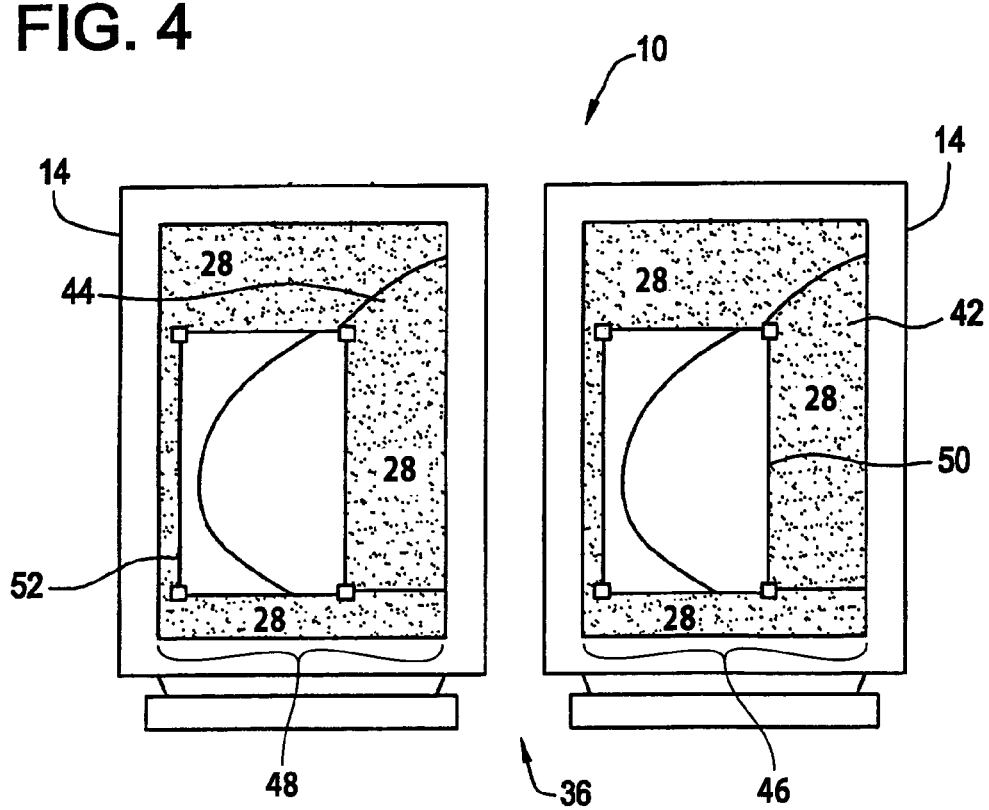
FIG. 4 is a schematic diagram showing dual display screens of a real-time masking system displaying two view ports synchronized based on a symmetrical synchronization configuration according to an exemplary embodiment.
Figure 5:
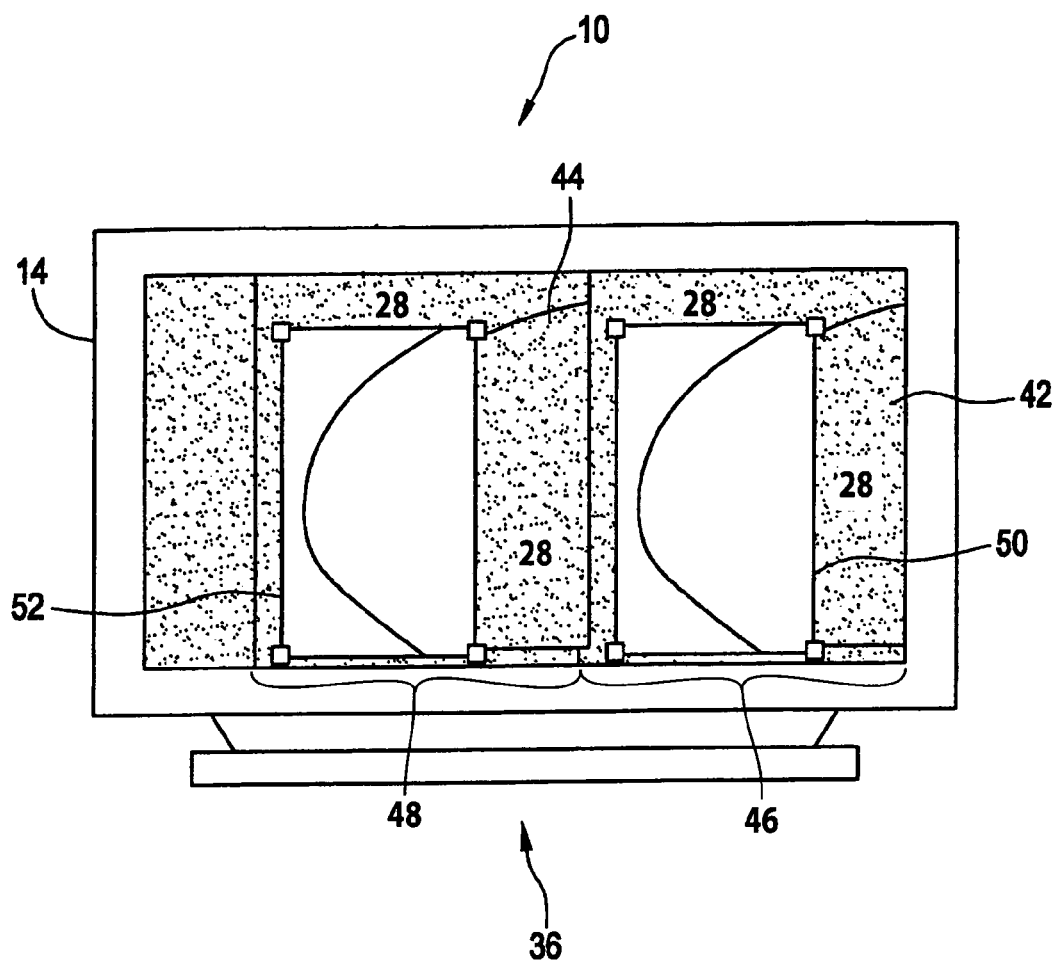
FIG. 5 is a schematic diagram showing a single display screen of a real-time masking system displaying two view ports synchronized based on a symmetrical synchronization configuration according to an exemplary embodiment.

Symmetrical synchronization configuration 136 allows a plurality of images 118 to be displayed symmetrically with respect to one another. As shown in FIGS. 4–5, display screen(s) 14 displays a first image 46 of a first object 42. Display screen(s) 14 also displays a first view port 50 that includes at least a portion of a first object 42. Further, display screen(s) 14 displays a second image 48 of a second object 44. Display screen(s) 14 also displays a second view port 52 that includes at least a portion of second object 44. Symmetrical synchronization configuration 36 orients first image 46 and second image 48 in a symmetrical relationship with one another. In addition, symmetrical synchronization configuration 36 configures the first image 46 and the second image 48 so that the movement of first view port 50 symmetrically correlates to the movement of second view port 52. In other words, symmetrical synchronization configuration 36 causes view port 50 and view port 52 to be linked in a way that results in one view port symmetrically corresponding to the actions of the other view port (e.g., movement, orientation, manipulation, etc.).

For example, as shown in FIG. 5, as first view port 50 is moved upward along a first object 42, the second view port 52 symmetrically (e.g., in parallel) moves upward along a second object 44. In addition, as first view port 50 is moved upward, the masked region 28 also moves to correspond to the new location of the first view port 50. In other words, the masked region 28 does not remain static and in fact moves relative to the new location of the first view port 50. This way, an operator can interactively select the areas to be viewed (and at the same time the areas to be masked) by moving the first view port around image 18. The mirror synchronization configuration 34 also configures the second view port 52 to symmetrically move around image 18 in response to any movement of the first view port 50. Therefore, the symmetrical synchronization configuration enables a user to view two objects in two view ports and/or two images as parallel images of one other. This feature is particularly useful for radiologists who must quickly compare adjacent current and/or historical images by comparing anatomical regions within the corresponding view ports 50 and 52. Rather than having to locate a landmark in one view port, note it and then take a similar location in the adjacent view port and note it, they have the ability to compare the symmetrical regions simultaneously. The radiologist can mask out extraneous regions and focus on specific areas without the contrast or brightness interference from other areas.

Figure 6:
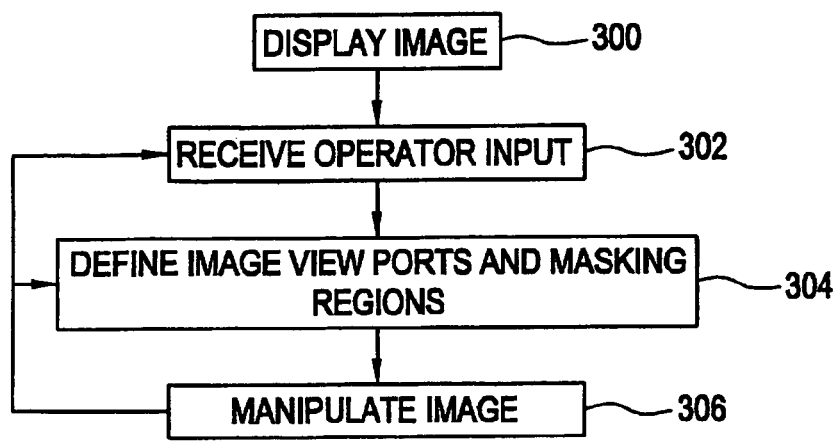
FIG. 6 is a flow chart showing a method of creating a mask and interactively navigating through an image in real-time according to an exemplary embodiment.

FIG. 6 is a flow diagram according to one embodiment of the invention. At least one image is displayed on at least one display screen at operation 300. Operator input is received to configure the at least one image at operation 302. A plurality of areas on the at least one image are defined as view ports at operation 304. The remaining areas on the at least one image are defined as masking regions at operation 304. The view ports and masking regions are configured according to at least one image manipulation function, including a real-time masking function at operation 306.

Figure 7:
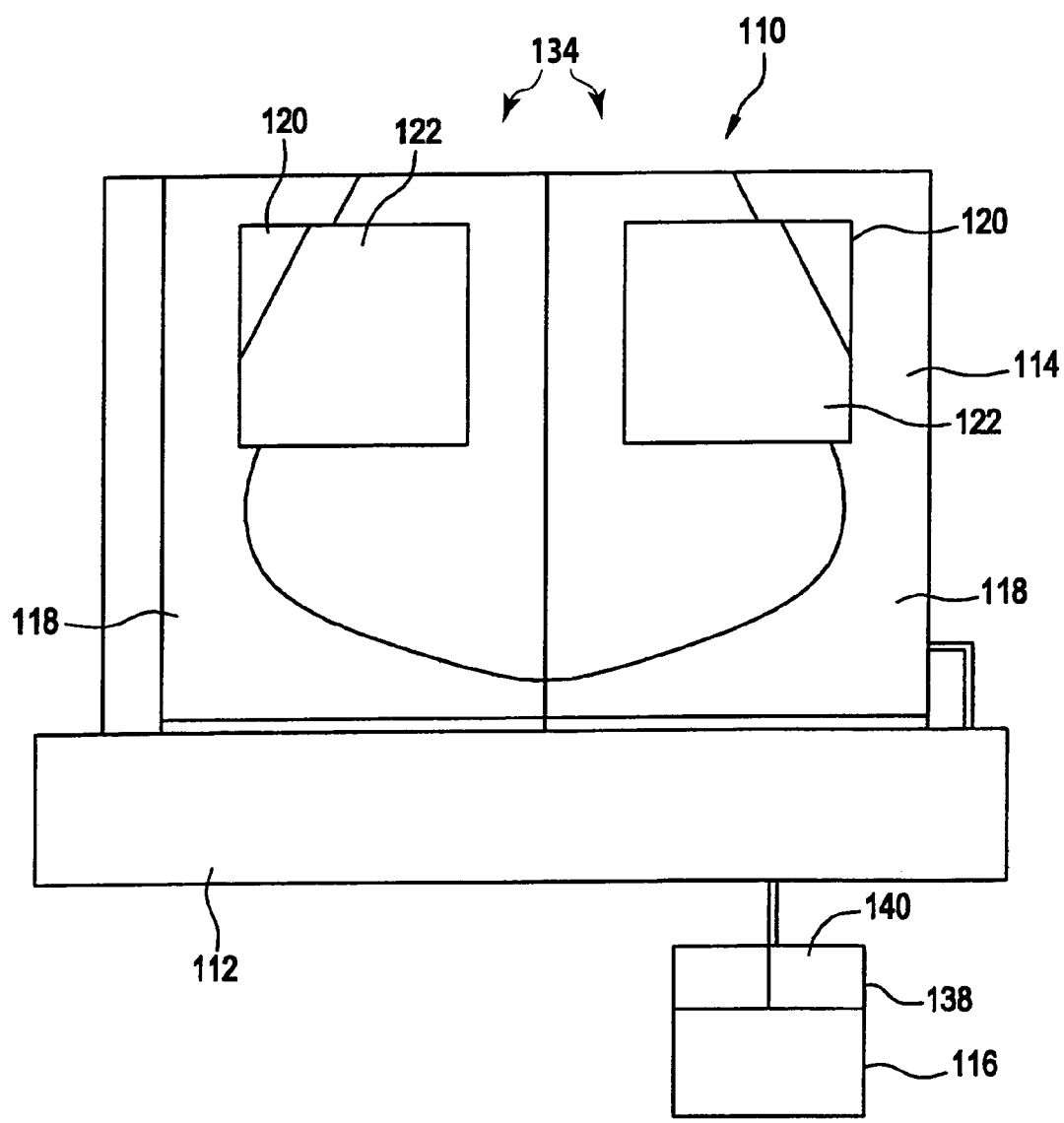
FIG. 7 is a schematic diagram showing an image manipulation system according to an exemplary embodiment.

Referring to FIG. 7, there is shown the major components of an image manipulation system according to another exemplary embodiment. FIG. 7 shows a computer device 112 for controlling the operation of the image manipulation system 110. At least one display screen 114 is coupled to computer device 112 for displaying a plurality of images 118. Images 118 may include many different types of objects such as generally similarly shaped objects, radiology images, mammography images, etc. Further, there are a plurality of view ports 120 within the plurality of images 118, that display at least a first portion 122 of the plurality of images 118. In addition, FIG. 7 shows an operator control device 116 for receiving operator input. Operator input is provided to computer device 112 to permit computer device 112 to control operation of the system in accordance with the operator input and at least one image manipulation functionl.

As shown in FIGS. 8–11, system 110 may include one display screen 114. In addition, system 110 may include a plurality of display screens 114 (e.g., 2 or more display screens). Further, the plurality of view ports 120 may be limited to only two view ports 120. Alternatively, the number of view ports 120 may be greater than 2.

Figure 8:
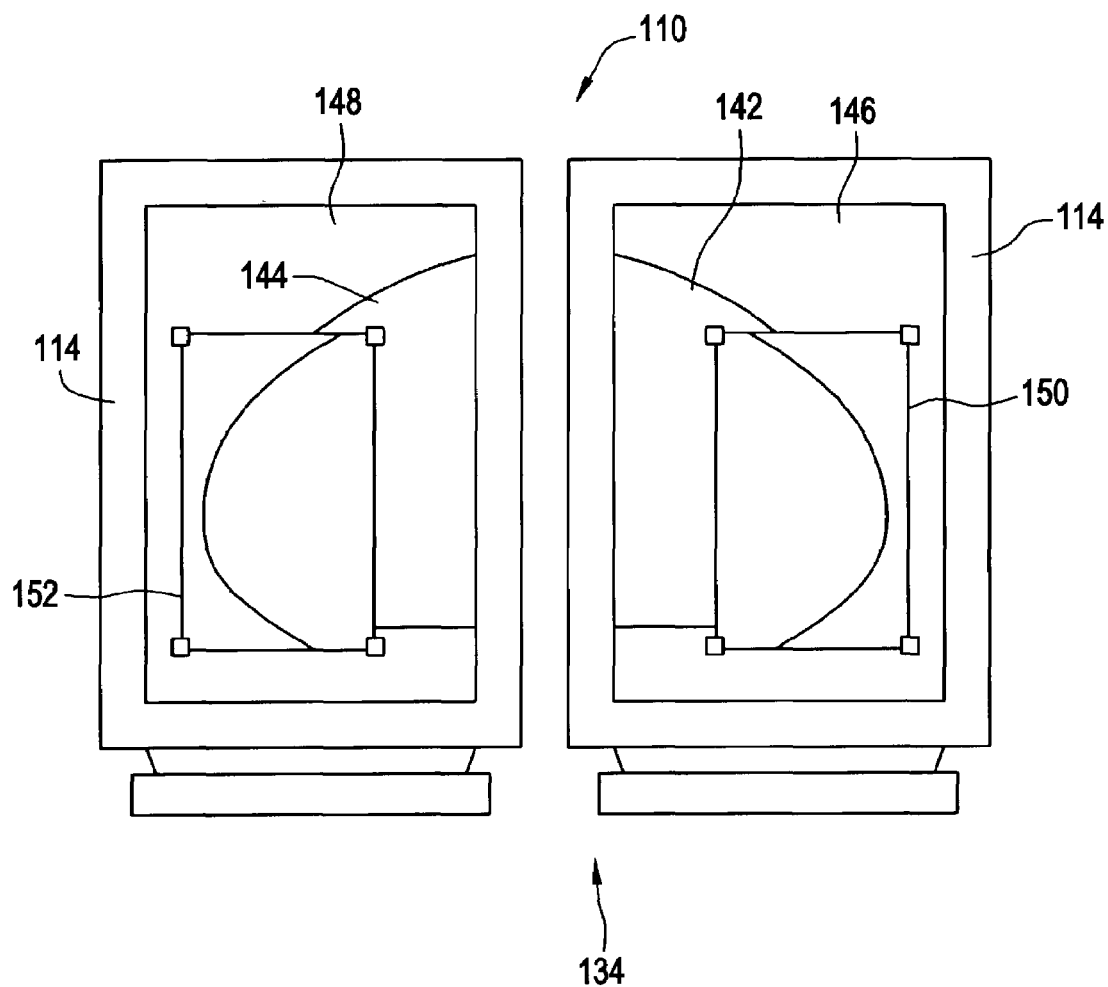
FIG. 8 is a schematic diagram showing dual display screens of an image manipulation system displaying two view ports synchronized based on a mirror synchronization configuration according to an exemplary embodiment.
Figure 9:
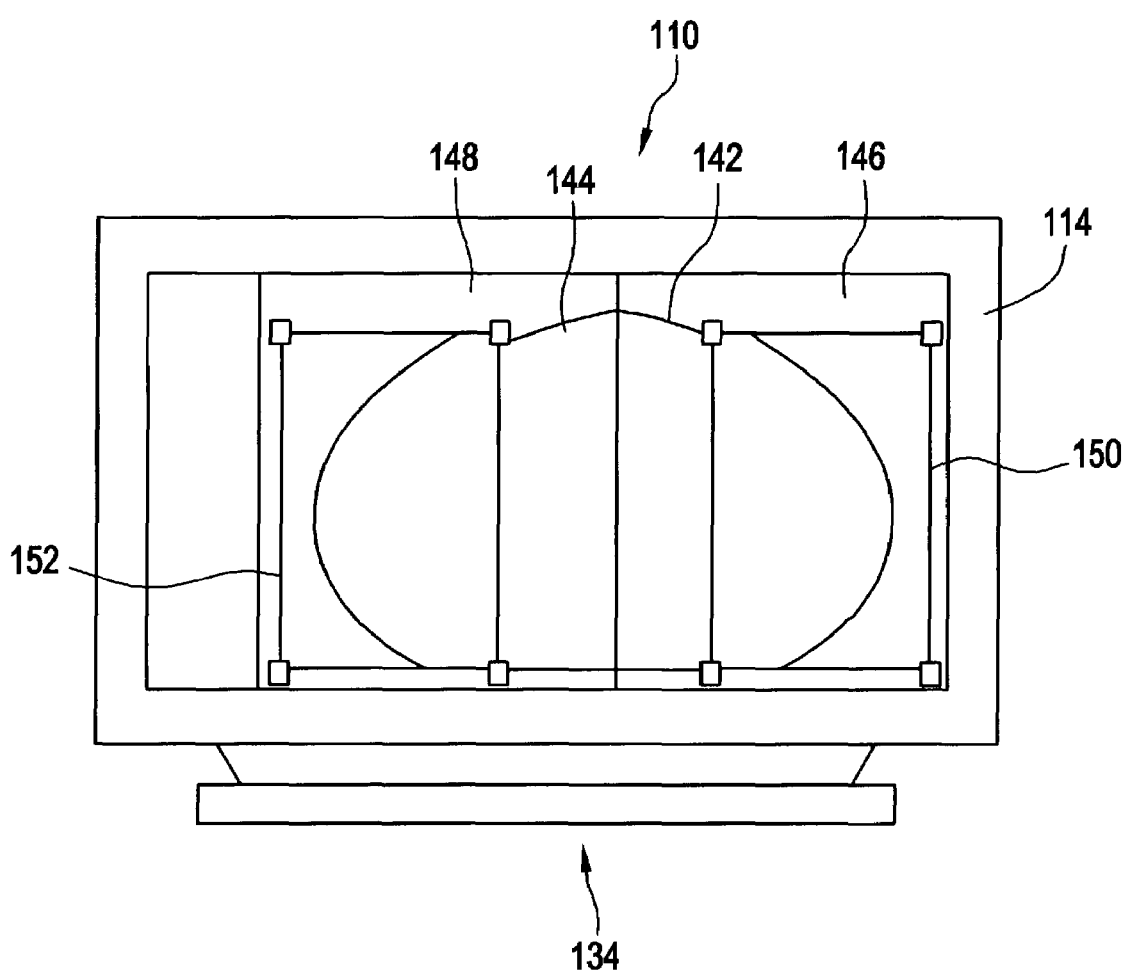
FIG. 9 is a schematic diagram showing a single display screen of an image manipulation system displaying two view ports synchronized based on a mirror synchronization configuration according to an exemplary embodiment.

The at least one image manipulation function synchronizes the plurality of view ports 120 according to either a mirror synchronization configuration 134 or a symmetrical synchronization configuration 136. Mirror synchronization configuration 134 allows a plurality of images 118 to be displayed as mirror images of one another. As shown in FIGS. 8–9, display screen(s) 114 displays a first image 146 of a first object 142. Display screen(s) 114 also displays a first view port 150 that includes at least a portion of first object 142. Further, display screen(s) 114 displays a second image 148 of a second object 144. Display screen(s) 114 also displays a second view port 152 that includes at least a portion of the second object 144. Mirror synchronization configuration 134 orients first image 146 and second image 148 in a mirrored relationship with one another. In addition, mirror synchronization configuration 134 configures first image 146 and the second image 148 so that the movement of first view port 150 mirroredly corresponds to the movement of second view port 152. In other words, mirror synchronization configuration 134 causes view port 150 and view port 152 to be linked in a way that results in one view port mirroring the actions of the other view port (e.g., movement, orientation, manipulation, etc.).

For example, as shown in FIG. 9 as first view port 150 is moved upward along a first object 142, the second view port 152 mirroredly (i.e., like a mirror image) moves upward along a second object 144. Therefore, the mirror synchronization configuration enables a user to view two objects in two view ports and/or two images as mirror images of each other. This feature is particularly useful for radiologists who must quickly compare adjacent current and/or historical images by comparing anatomical regions within the corresponding view ports 150 and 152. Rather than having to locate a landmark in one view port, note it and then take a similar location in the adjacent view port and note it, they have the ability to compare the mirrored regions simultaneously. The mirror synchronization configuration is especially useful for mammographers who are taught to scan right breast images counter clockwise and left breast images in a clockwise manner. Dual mirrored view ports 150 and 152 may be synchronized to scan adjacent breast images in adjacent view ports simultaneously side by side in orientations that are desired.

Figure 10:
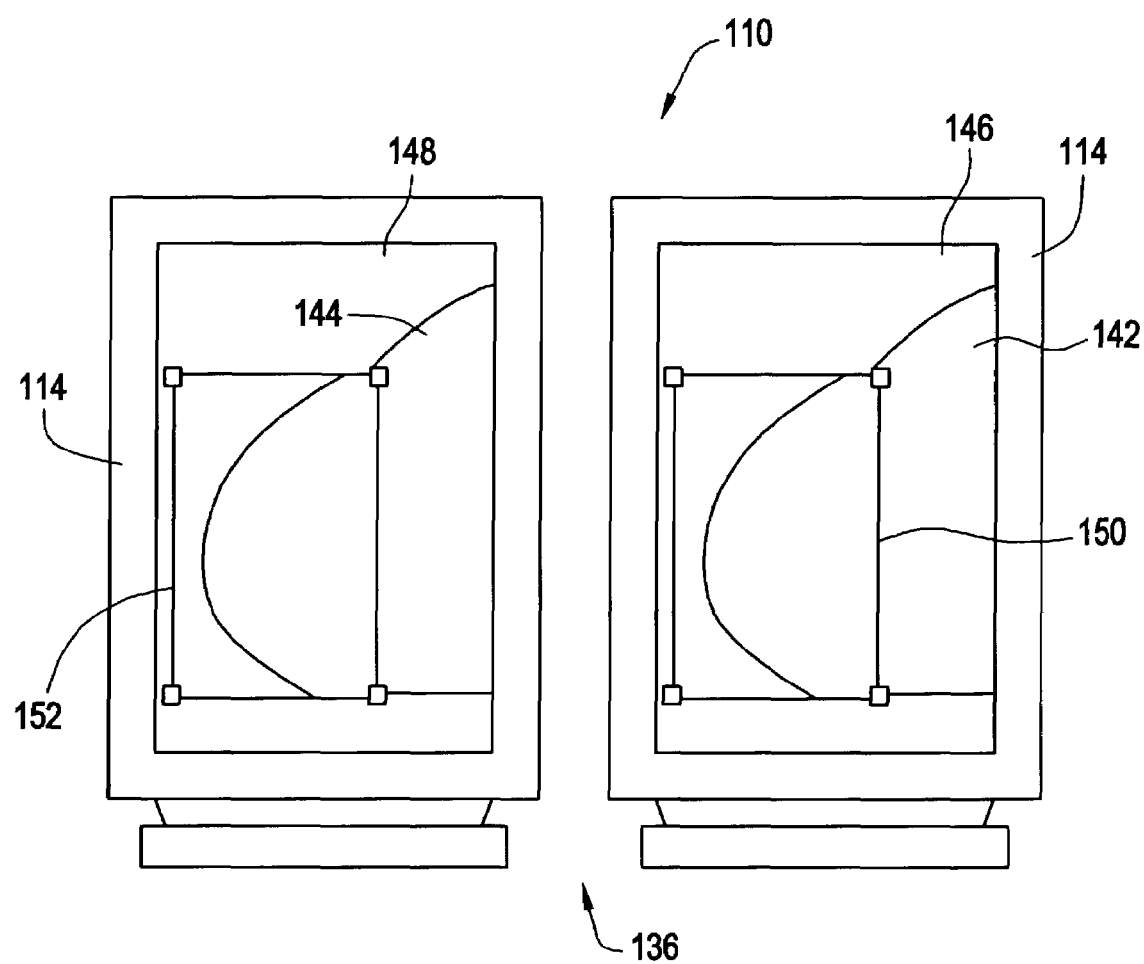
FIG. 10 is a schematic diagram showing dual display screens of an image manipulation system displaying two view ports synchronized based on a symmetrical synchronization configuration according to an exemplary embodiment.
Figure 11:
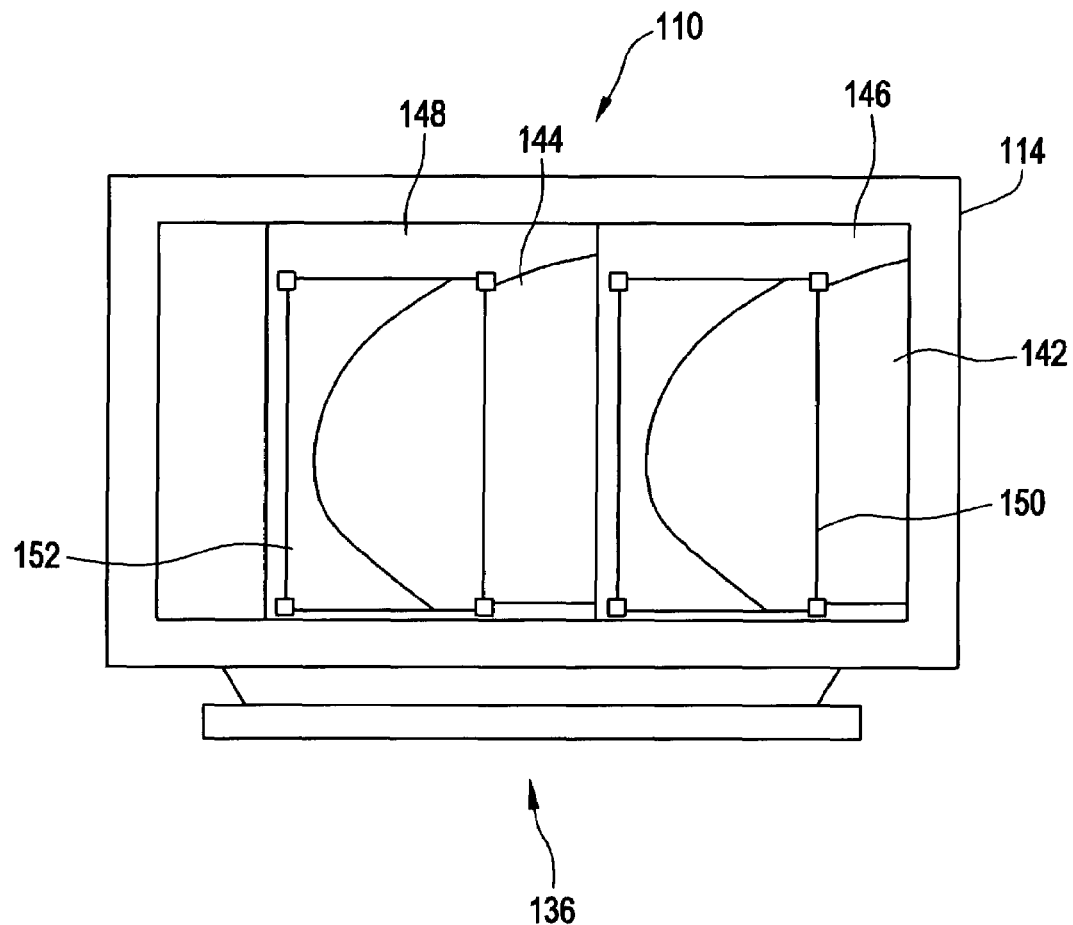
FIG. 11 is a schematic diagram showing a single display screen of an image manipulation system displaying two view ports synchronized based on a symmetrical synchronization configuration according to an exemplary embodiment.

Symmetrical synchronization configuration 136 allows a plurality of images 118 to be displayed symmetrically with respect to one another. As shown in FIGS. 10 & 11, display screen(s) 114 displays a first image 146 of a first object 142. Display screen(s) 114 also displays a first view port 150 that includes at least a portion of a first object 142. Further, display screen(s) 114 displays a second image 148 of a second object 144. Display screen(s) 114 also displays a second view port 152 that includes at least a portion of second object 144. Symmetrical synchronization configuration 136 orients first image 146 and second image 148 in a symmetrical relationship with one another. In addition, symmetrical synchronization configuration 136 configures the first image 146 and the second image 148 so that the movement of first view port 150 symmetrically correlates to the movement of second view port 152. In other words, symmetrical synchronization configuration 136 causes view port 150 and view port 152 to be linked in a way that results in one view port symmetrically corresponding to the actions of the other view port (e.g., movement, orientation, manipulation, etc.).

For example, as shown in FIG. 11, as first view port 150 is moved upward along a first object 142, the second view port 152 symmetrically (e.g., in parallel) moves upward along a second object 144. Therefore, the symmetrical synchronization configuration enables a user to view two objects in two view ports and/or two images as parallel images of one other. This feature is particularly useful for radiologists who must quickly compare adjacent current and/or historical images by comparing anatomical regions within the corresponding view ports 150 and 152. Rather than having to locate a landmark in one view port, note it and then take a similar location in the adjacent view port and note it, they have the ability to compare the symmetrical regions simultaneously. The symmetrical synchronization configuration is especially useful for mammographers who are taught to scan right and left breast images in consideration of one another. Dual symmetrical view ports 150 and 152 may be synchronized to scan adjacent breast images in adjacent view ports simultaneously side by side in orientations as that are desired.

System 110 may also include numerous image manipulation functions. For example, system 110 may include a zoom function for zooming in toward and out from at least a portion of the plurality of images 118 within the at least one display screen 114. System 110 may also include a magnification function for magnifying at least a portion of the plurality of images 118 within the at least one display screen 114. System 110 may also include a sizing function for increasing or decreasing the size of the plurality of view ports 120. The zoom function, magnification function, and sizing function are generally controlled by user inputs through the operator control device 116. For example, operator control device 116 may include a computer mouse device 138 having at least a right button 140. The image manipulation functions could be configured differently depending on a user by depressing the right button 140 on the computer mouse device 138. Furthermore, system 110 is configured so that any of the image manipulation functions may be conducted interactively in real-time.

Figure 12:
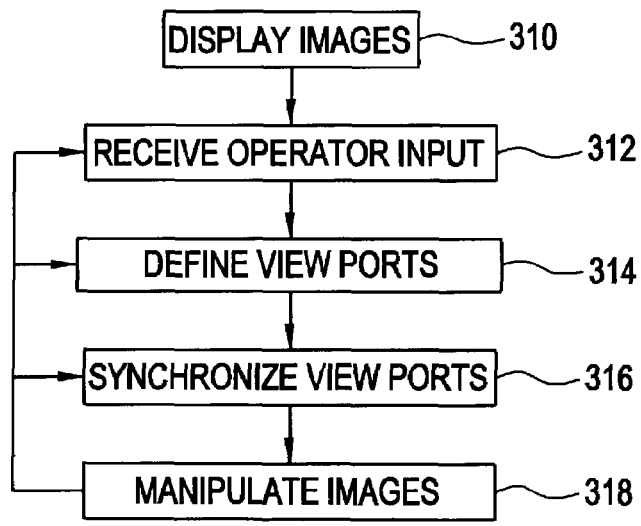
FIG. 12 is a flow chart showing a method of manipulating an image according to an exemplary embodiment.

FIG. 12 is a flow diagram according to one embodiment of the invention. A plurality of generally similarly shaped objects are displayed on at least one display screen at operation 310. Operator input is received to configure the plurality of generally similarly shaped objects at operation 312. A plurality of areas on the plurality of generally similarly shaped objects are defined as view ports at operation 314. The view ports are synchronized according to a synchronization configuration including either mirror synchronization or symmetrical synchronization at operation 316. Further, the plurality of generally similarly shaped objects are manipulated according to at least one image manipulation function at operation 318. The at least one image manipulation function may include a zoom function for zooming in toward or out from at least a portion of the plurality of generally similarly shaped objects. The at least one image manipulation function may also include a magnification function for magnifying at least a portion of the plurality of generally similarly shaped objects. In addition, the at least one image manipulation function may include a sizing function for increasing or decreasing the size of at least a portion of the plurality of generally similarly shaped objects. It is understood that the at least one image manipulation function may include any other suitable manipulation function.

While the embodiments and application of the invention illustrated in the figures and described above are presently preferred, it should be understood that these embodiments are offered by way of example only. Accordingly, the present invention is not limited to a particular embodiment, but extends to various modifications that nevertheless fall within the scope of this application.

What is claimed is:

1. An image manipulation system comprising:
   a computer device for controlling operation of said system;
   at least one display screen coupled to the computer device for displaying a plurality of generally similarly shaped objects, the plurality of generally similarly shaped objects include a plurality of view ports that display at least a portion of the plurality of generally similarly shaped objects;

an operator control device coupled to the computer device for receiving operator input, the operator input being provided to the computer device to permit the computer device to control operation of the system in accordance with the operator input and at least one image manipulation function, the at least one image manipulation function synchronizes the plurality of view ports according to either a mirror synchronization configuration or a symmetrical synchronization configuration; and a real-time masking function, wherein the real-time masking function permits at least one masking region to be reconfigured in real-time while continuously displaying the plurality of view ports.

2. The system of claim 1, wherein the at least one image manipulation function comprises at least one of the following functions:

a zoom function for zooming in toward and out from the at least a portion of the plurality of generally similarly shaped objects within the plurality of view ports;

a magnification function for magnifying the at least a portion of the plurality of generally similarly shaped objects within the plurality of view ports; or at least one sizing function for increasing or decreasing the size of the plurality of view ports.

3. The system of claim 2, wherein the plurality of view ports consists of two view ports.

4. The system of claim 3, wherein the at least one display screen consists of one display screen.

5. The system of claim 3, wherein the at least one display screen consists of two display screens.

6. The system of claim 2, wherein the at least one image manipulation function can be configured differently depending on a user.

7. The system of claim 2, wherein the operator control device comprises a computer mouse device having at least a right button.

8. The system of claim 7, wherein the at least one image manipulation function is configured by depressing the right button on the computer mouse device.

9. The system of claim 2, wherein the at least one image manipulation function is interactive and conducted in real-time.

10. An image manipulation system comprising:

a computer device for controlling operation of said system;

at least one display screen coupled to the computer device for displaying a plurality of mammography images, the plurality of mammography images include a plurality of view ports that display at least a portion of the plurality of mammography images;

an operator control device coupled to the computer device for receiving operator input, the operator input being provided to the computer device to permit the computer device to control operation of the system in accordance with the operator input and at least one image manipulation function, the at least one image manipulation function synchronizes the plurality of view ports according to a mirror synchronization configuration; and a real-time masking function, wherein the real-time masking function permits at least one masking region to be reconfigured in real-time while continuously displaying the plurality of view ports.

11. The system of claim 10, wherein the mirror synchronization configuration allows the plurality of mammography images to be displayed in a mirrored relationship with one another, and configured so that movement of a first view port mirroredly corresponds to movement of a second view port, thereby enabling corresponding mirrored portions of the plurality of mammography images to be viewed simultaneously.

12. The system of claim 11, wherein the at least one image manipulation function comprises at least one of the following functions:

a zoom function for zooming in toward and out from the at least a portion of the plurality of mammography images within the plurality of view ports;

a magnification function for magnifying the at least a portion of the plurality of mammography images within the plurality of view ports; or at least one sizing function for increasing or decreasing the size of the plurality of view ports.

13. The system of claim 12, wherein the plurality of view ports consists of two view ports.

14. The system of claim 13, wherein the at least one display screen consists of one display screen.

15. The system of claim 13, wherein the at least one display screen consists of two display screens.

16. The system of claim 12, wherein the at least one image manipulation function can be configured differently depending on a user.

17. The system of claim 12, wherein the at least one image manipulation function is interactive and conducted in real-time.

18. An image manipulation system comprising:

a computer device for controlling operation of said system;

at least one display screen coupled to the computer device for displaying a plurality of mammography images, the plurality of mammography images include a plurality of view ports that display at least a portion of the plurality of mammography images;

an operator control device coupled to the computer device for receiving operator input, the operator input being provided to the computer device to permit the computer device to control operation of the system in accordance with the operator input and at least one image manipulation function, the at least one image manipulation function synchronizes the plurality of view ports according to a symmetrical synchronization configuration; and a real-time masking function, wherein the real-time masking function permits at least one masking region to be reconfigured in real-time while continuously displaying the plurality of view ports.

19. The system of claim 18, wherein the symmetrical synchronization configuration allows the plurality of mammography images to be displayed in a symmetrical relationship with one another, and configured so that movement of a first view port symmetrically corresponds to movement of a second view port, thereby enabling corresponding symmetrical portions of the plurality of mammography images to be viewed simultaneously.

20. The system of claim 19, wherein the at least one image manipulation function comprises at least one of the following functions:

a zoom function for zooming in toward and out from the at least a portion of the plurality of mammography images within the plurality of view ports;

a magnification function for magnifying the at least a portion of the plurality of mammography images within the plurality of view ports; or at least one sizing function for increasing or decreasing the size of the plurality of view ports.

21. The system of claim 20, wherein the plurality of view ports consists of two view ports.

22. The system of claim 21, wherein the at least one display screen consists of one display screen.

23. The system of claim 21, wherein the at least one display screen consists of two display screens.

24. The system of claim 20, wherein the at least one image manipulation function can be configured differently depending on a user.

25. The system of claim 20, wherein the at least one image manipulation function is interactive and conducted in real-time.

26. A method of manipulating an image, comprising:

displaying a plurality of generally similarly shaped objects on at least one display screen;

receiving operator input, the operator input being used to configure the plurality of generally similarly shaped objects;

defining a plurality of areas on the plurality of generally similarly shaped objects as view ports, wherein the view ports are defined by a plurality of masking regions, the plurality of masking regions being configurable in real-time while continuously displaying the view ports;

synchronizing the view ports according to a synchronization configuration including either mirror synchronization or symmetrical synchronization; and manipulating the plurality of generally similarly shaped objects according to at least one image manipulation function.

27. The method of claim 26, wherein the at least one image manipulation function comprises at least one of the following functions:

a zoom function for zooming in toward or out from at least a portion of the plurality of generally similarly shaped objects;

a magnification function for magnifying the at least a portion of the plurality of generally similarly shaped objects; or a sizing function for increasing or decreasing the size of the at least a portion of the plurality of generally similarly shaped objects.

28. An image manipulation system comprising:

means for controlling the operation of said system;

means for displaying a plurality of generally similarly shaped objects;

means for displaying a plurality of view ports, said plurality of view ports displaying at least a portion of the generally similarly shaped objects, wherein the view ports are defined by a plurality of masking regions, the pluraliw of masking regions being configurable in real-time while continuously displaying the view ports;

means for receiving operator input;

means for manipulating the plurality of generally similarly shaped objects according to the operator input; and means for synchronizing the plurality of view ports according to either a mirror synchronization configuration or a symmetrical synchronization configuration.

29. The system of claim 28, wherein the operator input comprises at least one of the following functions:

zoom input for zooming in toward and out from at least a portion of the plurality of generally similarly shaped objects;

magnification input for magnifying the at least a portion of the plurality of generally similarly shaped objects; or sizing input for increasing or decreasing the size of the plurality of view ports.

30. The system of claim 29, wherein the at least one image manipulation function is interactive and conducted in real-time.

* * * * *

UNITED STATES PATENT AND TRADEMARK OFFICE
CERTIFICATE OF CORRECTION

PATENT NO. : 7,127,684 B2  Page 1 of 1
APPLICATION NO. : 10/304352
DATED : October 24, 2006
INVENTOR(S) : Mark M. Morita et al.

It is certified that error appears in the above-identified patent and that said Letters Patent is hereby corrected as shown below:

On Title Page, Item (73)
Assignee is listed as GE Informational Systems Technologies, Inc., Milwaukee, WI (US). Should be, assignee is GE Medical Systems Information Technologies, Inc., Milwaukee, WI (US)

Signed and Sealed this

Ninth Day of January, 2007

JON W. DUDAS
*Director of the United States Patent and Trademark Office*